(12) United States Patent
Bardon et al.

(10) Patent No.: US 10,864,491 B2
(45) Date of Patent: Dec. 15, 2020

(54) PLANT FOR PRODUCING A COMPOSITION COMPRISING DROPS AND ASSOCIATED PRODUCTION PROCESS

(71) Applicant: CAPSUM, Marseilles (FR)

(72) Inventors: Sébastien Bardon, Paris (FR); Mathieu Goutayer, Saint Malo (FR); Yan Eric Pafumi, Gardanne (FR)

(73) Assignee: CAPSUM, Marseilles (FR)

( * ) Notice: Subject to any disclaimer, the term of this patent is extended or adjusted under 35 U.S.C. 154(b) by 0 days.

(21) Appl. No.: 16/333,244

(22) PCT Filed: Sep. 13, 2017

(86) PCT No.: PCT/EP2017/072978
§ 371 (c)(1),
(2) Date: Mar. 14, 2019

(87) PCT Pub. No.: WO2018/050675
PCT Pub. Date: Mar. 22, 2018

(65) Prior Publication Data
US 2019/0247811 A1 Aug. 15, 2019

(30) Foreign Application Priority Data
Sep. 14, 2016 (FR) ...................... 16 58602

(51) Int. Cl.
*B01F 13/10* (2006.01)
*A61K 8/03* (2006.01)
(Continued)

(52) U.S. Cl.
CPC ............ *B01F 13/1061* (2013.01); *A61K 8/03* (2013.01); *A61K 8/11* (2013.01); *A61Q 13/00* (2013.01);
(Continued)

(58) Field of Classification Search
None
See application file for complete search history.

(56) References Cited

U.S. PATENT DOCUMENTS

2005/0087562 A1* 4/2005 Koide ................. B67D 1/0044
222/252
2016/0250611 A1* 9/2016 Goutayer ................ A23P 10/30
264/4.1

FOREIGN PATENT DOCUMENTS

DE 10 2006 049054 A1 4/2008
FR 3041252 9/2015
(Continued)

OTHER PUBLICATIONS

Preliminary Research Report dated Jun. 13, 2017 in related French Patent Application No. 16 58602.
(Continued)

*Primary Examiner* — Jeffrey D Washville
(74) *Attorney, Agent, or Firm* — Pearne & Gordon LLP

(57) ABSTRACT

The present invention relates to a plant (2) for producing a composition (9), in particular a cosmetic composition, comprising drops (8) of at least one first fluid dispersed in a second fluid substantially immiscible with the first fluid, each drop (8) comprising a core formed of the first fluid, and optionally a shell suitable for retaining the core, the plant (2) comprising:
  a device (16) for producing the composition (9),
  a storage module (10) comprising:
    at least one tank (36) for storing at least one first stock solution (A), and at least one tank (38) for storing at least one first solution of active agent(s),
    at least one tank (40) for storing at least one second stock solution (B), and (Continued)

Figure 1:
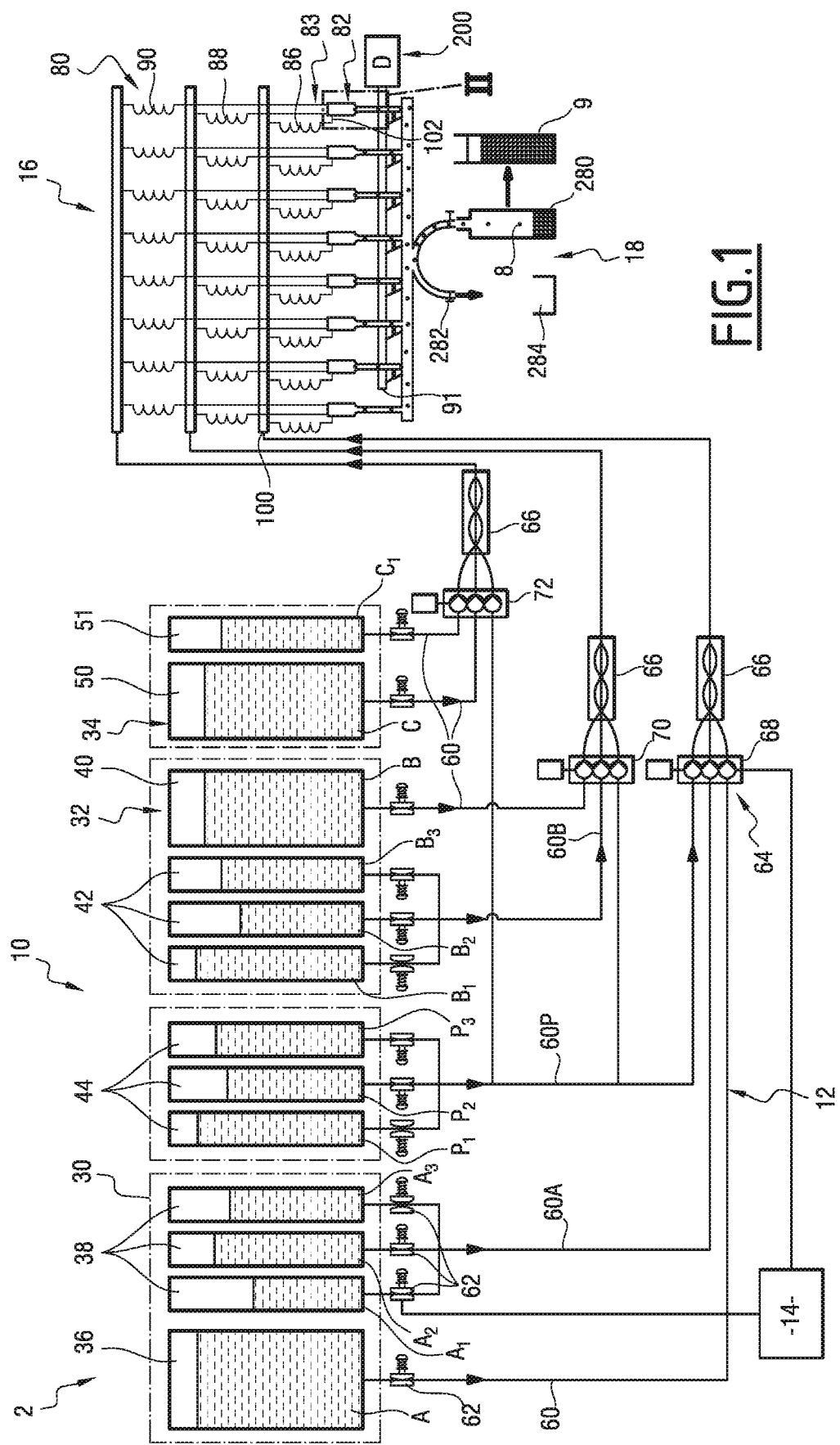

a preparation module (12), connected to the storage module (10).

23 Claims, 2 Drawing Sheets

(51) Int. Cl.
- *A61K 8/11* (2006.01)
- *A61Q 13/00* (2006.01)
- *B01F 3/08* (2006.01)
- *B01F 13/00* (2006.01)

(52) U.S. Cl.
CPC .......... *B01F 3/0807* (2013.01); *B01F 3/0811* (2013.01); *B01F 13/0062* (2013.01); *B01F 2003/0834* (2013.01); *B01F 2003/0842* (2013.01); *B01F 2215/0031* (2013.01)

(56) References Cited

FOREIGN PATENT DOCUMENTS

| | | |
|---|---|---|
| FR | 3047662 | 2/2016 |
| WO | WO 2012/120043 A2 | 9/2012 |
| WO | WO 2014/138154 A1 | 9/2014 |
| WO | WO 2015/055839 A1 | 4/2015 |

OTHER PUBLICATIONS

International Search Report dated Dec. 22, 2017 in related International Patent Application No. PCT/EP2017/072978.
Written Opinion in related International Patent Application No. PCT/EP2017/072978.
International Preliminary Report on Patentabiliy in related International Patent Application No. PCT/EP2017/072978.

\* cited by examiner

PLANT FOR PRODUCING A COMPOSITION COMPRISING DROPS AND ASSOCIATED PRODUCTION PROCESS

The present invention relates to a plant for producing a composition, in particular a cosmetic composition, which comprises drops of at least one first fluid dispersed in a second fluid that is substantially immiscible with the first fluid, wherein each drop comprises a core formed by the first fluid and optionally a shell to hold the core.

Historically, the cosmetics industry has given consumers a wide range of choices for active agents, colors (including tones, shades or hues) and textures. In a typical scenario, these products are prepackaged according to a predetermined choice in terms of nature and quantities of raw materials and, therefore, in terms of, inter alia, color, active agents and texture.

Because of this manufacturing system, points of sale only offer a finite number of selections for the consumer. Therefore, the choice of the consumer is limited by the current availability and/or the specific choices made in advance by the manufacturer.

In parallel, systems are known from the prior art for producing compositions in the form of an emulsion or dispersion, and, in particular, comprising drops of different fluids forming the dispersed (or internal) and continuous (or external) phases. Such emulsions/dispersions may, in particular, be obtained by using microfluidic processes that are known to confer on them a particularly interesting visual and/or changing texture.

However, such production systems are not suitable for producing customized compositions related to the needs of consumers and, moreover, directly at the points of sale.

An object of the invention is to provide a plant for production of a composition in the form of an emulsion/dispersion as described above, that is autonomous, fast and easily adjustable to the meet the needs of a user.

In particular, an object of the invention is to provide a production facility for the customization (or personalization) of compositions, especially cosmetic, in the form of an emulsion or dispersion, and, in particular, that are obtained by a microfluidic process, directly by the consumer at the points of sale.

For this purpose, the object of the invention is a plant of the aforementioned type, wherein the plant comprises:
  a device for producing the composition,
  a storage module comprising:
    at least one storage tank for at least a first stock solution, and at least one storage tank for at least a first solution of active agent(s) and/or additional compound(s),
    at least one storage tank for at least one second stock solution and, optionally, at least one storage tank for at least one second solution of active agent(s) and/or additional compound(s), and
    optionally, at least one storage tank for at least a third stock solution and, optionally, at least one storage tank for at least a third solution of active agent(s) and/or additional compound(s),
  a preparation module, connected to the storage module, and designed to prepare at least:
    the first fluid by mixing determined quantities of the first stock solution and at least the first solution of active agent(s) and/or additional compound(s),
    the second fluid by mixing determined quantities of the second stock solution and, optionally, at least the second solution of active agent(s) and/or additional compound(s),
    optionally, an intermediate fluid by mixing determined quantities of the third stock solution and, optionally, at least the third solution of active agent(s) and/or additional compound(s);
  wherein the preparation module is designed to convey the first fluid, the second fluid and, optionally, the intermediate fluid in the production device,
  a control unit designed for:
    determining the quantity of one or more first solutions of active agent(s) and/or of additional compound(s) to be mixed with a determined quantity of the first stock solution to obtain the first fluid,
    optionally, determining the quantity of one or more second solutions of active agent(s) and/or additional compound(s) to be mixed with a determined quantity of the second stock solution to obtain the second fluid,
    optionally, determining the quantity of the third stock solution of active agent(s) to be mixed with a determined quantity of one or more third solutions of active agent(s) and/or additional compound(s) to obtain the intermediate fluid.

The plant according to the invention may comprise one or more of the following characteristics, taken separately or in any technically feasible combination:
  the storage module further comprises at least one storage tank for at least one perfume solution, wherein the preparation module is capable of adding a determined quantity of the perfume solution(s) to the first fluid and/or to the second fluid and/or to the intermediate fluid, preferably in the first fluid;
  the storage module comprises several tanks containing several first solutions of active agent(s) and/or additional compound(s) and/or several tanks containing several second solutions of active agents and/or additional compound(s), and optionally several tanks containing several third solutions of active and/or additional compound(s), and/or several tanks containing several perfume solutions,
  wherein the preparation module is able to mix selectively:
  a predetermined quantity of one or more first solutions of active agent(s) and/or of additional compound(s) with a determined quantity of the first stock solution and, optionally, a determined quantity of one or more perfume solutions, to form the first fluid,
  a determined quantity of one or more second solutions of active agent(s) and/or additional compound(s) with a determined quantity of the second stock solution and, optionally, a determined quantity of one or more perfume solutions, to form the second fluid,
  optionally, a determined quantity of one or more third solutions of active agent(s) and/or additional compound(s) with a determined quantity of third stock solution and, optionally, a determined quantity of one or more perfume solutions(s) to form the intermediate fluid;
  each storage tank of the storage module is removable;
  the preparation module comprises selection valves for each solution to be mixed in order to obtain at least the first fluid, the second fluid, and, where appropriate, the intermediate fluid;
  the preparation module comprises at least one static mixer, wherein each static mixer is designed to homogenize the mixtures to form the first fluid, the second fluid and/or, if appropriate, the intermediate fluid;

the production device comprises at least one element chosen from among:
- a nozzle, preferably comprising a hollow body delimiting an internal duct and an external duct extending along a vertical longitudinal axis and arranged coaxially along this longitudinal axis, wherein the external duct opens downwards through a drop-forming opening, wherein the nozzle comprises an external feed path for the first fluid, an external feed path for the second fluid, and, optionally, an external feed path for the intermediate fluid, wherein the external feed paths, and optionally, the formation nozzle, are connected to the inner duct, while the external supply ducts are connected to the external duct,
- a mixer provided with at least one dispersion module, in particular at least one dispersion turbine, and
- a static mixer;

the production device comprises at least a plurality of nozzles, wherein each first and second rail, and, where appropriate, each third rail, is connected to the plurality of nozzles, preferably wherein the nozzles are arranged parallel to each other;

each distribution rail is connected to the corresponding nozzle by a connection forming a pressure drop;

the plant comprises a collector connected to the production device and capable of collecting the composition;

the production device and/or the collector, preferably the production device, comprises at least one device for injecting a solution to increase the viscosity of the second fluid;

a viscosity-increase solution delivery rail is connected to each nozzle in order to inject the solution for increasing the viscosity in the second fluid after the drop formation.

The invention furthermore relates to a method for producing a composition, in particular a cosmetic composition, comprising drops of at least one first fluid dispersed in a second fluid that is substantially immiscible with the first fluid, wherein each drop comprises a core formed of the first fluid, and, optionally, a shell designed to retain the core, from a plant according to any one of the preceding claims, wherein the method comprises:

preparation, in the preparation module:
- of the first fluid by mixing determined quantities of the first stock solution and at least a first solution of active agent(s) and/or additional compound(s) and/or optionally at least one perfume solution,
- of the second fluid by mixing determined quantities of the second stock solution and, optionally, at least a second solution of active agent(s) and/or of additional compound(s) and/or at least one perfume solution, and
- optionally, of the intermediate fluid by mixing determined quantities of the third stock solution and, optionally, at least a third solution of active agent(s) and/or additional compound(s) and/or optionally, at least one perfume solution, the simultaneous or sequential conveying of the first fluid, the second fluid and, if appropriate, the intermediate fluid in the production device, and the formation of a composition by the production device.

The method according to the invention may comprise one or more of the following characteristics, taken separately or in any technically feasible combination:

the method further comprises, after the step of forming the composition:
- the preparation in the same preparation module of at least one additional fluid different from the first fluid and/or at least one second additional fluid different from the second fluid and/or, optionally, at least one additional intermediate fluid different from the intermediate fluid,
- the simultaneous or sequential conveying of the first additional fluid, the second additional fluid and, optionally, the third additional fluid in the production device, and
- the formation of an additional composition by the production device;

the method further comprises, after the step of forming the composition, a step of injecting a solution to increase the viscosity of the composition, in particular the second fluid.

The invention also relates to the use of a plant as defined above for the personalization of a composition, in particular a cosmetic composition, by the consumer.

In the context of the present invention, the above-mentioned compositions may be referred to interchangeably as "dispersions" or "emulsions".

A drop according to the invention is composed of a core, also called the interior of the drop, where appropriate surrounded by a shell, which isolates the interior of the drop from the continuous phase of the emulsion.

According to one embodiment, the compositions according to the invention do not comprise a surfactant. They are therefore different from the usual cosmetic emulsions/dispersions.

Figure 2:
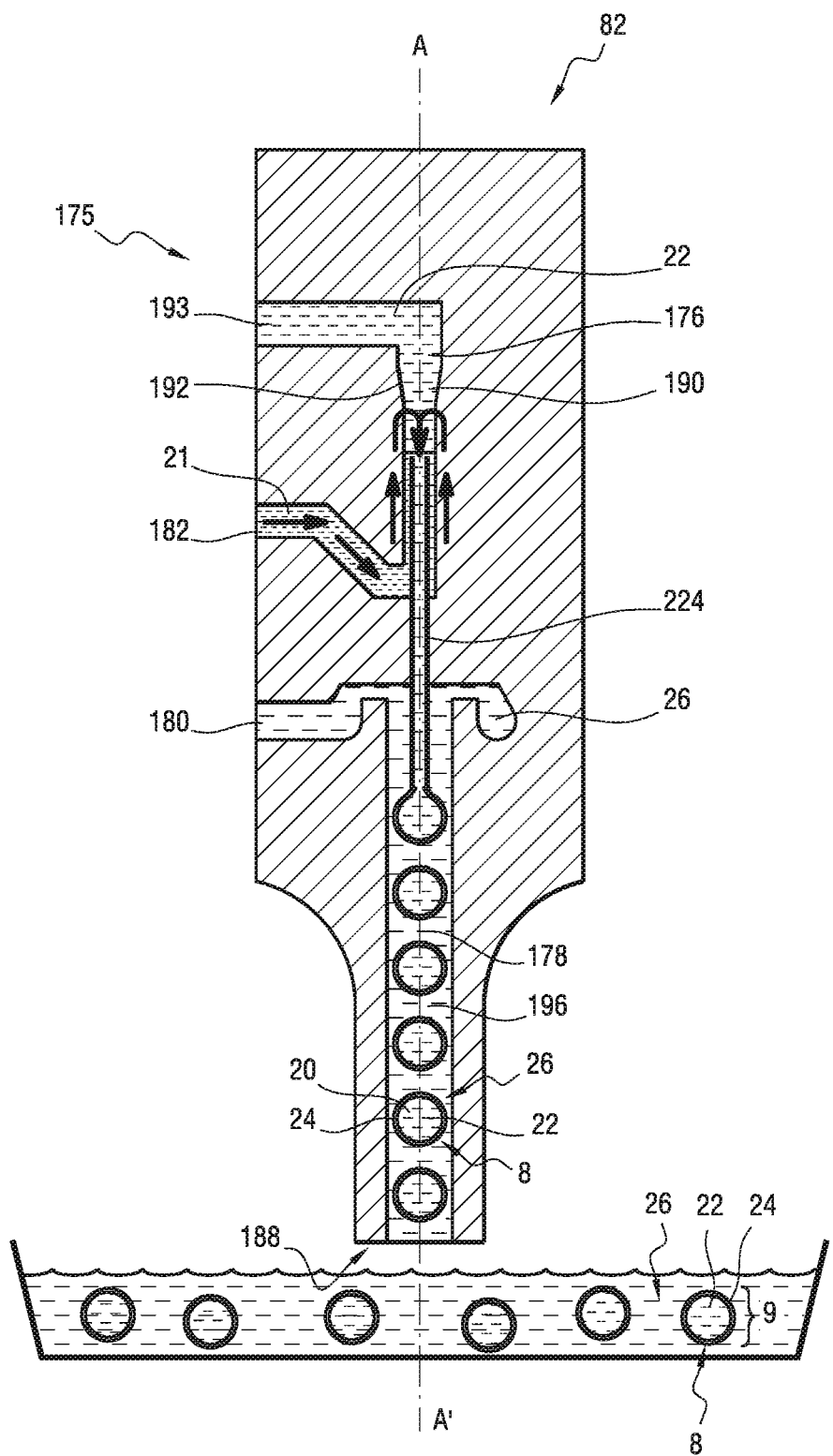

The invention will be better understood upon reading the description which follows, given solely by way of example, and with reference to the appended drawings, wherein:

FIG. 1 shows a schematic view of a plant for producing a composition comprising drops according to the invention, and FIG. 2 shows a sectional view of a nozzle, namely a particular embodiment of a device for producing the composition of the plant of FIG. 1.

In what follows, the terms "upstream" and "downstream" refer to the normal direction of circulation of a fluid, and the terms "upper" and "lower" are understood in relation to the orientations represented on the figures.

An example of a plant 2 for producing a composition 9, in particular a cosmetic composition, comprising dispersed elements 8 according to the invention, is illustrated in FIG. 1.

This plant 2 comprises a fluid storage module 10, a fluid preparation module 12, a control unit 14, a device 16 for producing a composition 9 comprising dispersed elements 8 (or drops), and a collector 18 of the composition 9.

The production plant 2 is intended to produce a composition 9 in the form of an emulsion, and therefore comprising dispersed elements 8, for example dispersed elements 8 like those shown in FIG. 2. In this FIG. 2, each dispersed element 8 comprises a core 20 comprising at least a first fluid 22 and a shell 24 that is designed to retain the core 20 in a second fluid 26.

According to a particular embodiment, a composition according to the invention can remain stable over time without necessarily having recourse to the presence of a shell (or membrane) at the continuous phase/dispersed phase interface.

In the embodiment illustrated in FIG. 2, the dispersed elements are drops 8. The production plant 2 is intended to form a drop dispersion 8 of the type described in the application WO 2012/120043. The dispersion of drops 8 is formed of at least a first fluid 22 forming a first phase dispersed in a second fluid 26, while the second fluid 26 forms a second continuous phase that is substantially immiscible with the first phase.

The first phase forming the drops 8 (i.e. dispersed or internal phase) is preferably an oily phase, while the second phase in which the drops 8 are dispersed (i.e. continuous or external phase) is preferably an aqueous phase, or vice versa. The oily phase is immiscible with the aqueous phase.

The oily phase comprises at least one oil; at least one gelling agent, in particular chosen from organic or inorganic, polymeric or molecular lipophilic gelling agents; fatty substances solid at ambient temperature and pressure; and their mixtures.

As oil(s) may be mentioned, for example, a silicone oil, a synthetic oil, a mineral oil, a vegetable oil or a mixture of these oils.

Examples of gelling agents that may be mentioned include those described in FR1558850, the contents of which are incorporated by reference.

The presence of gelling agent(s), especially when present in the first fluid 22, is advantageous in that the resulting composition 9 has a different texture and/or improved mechanical strength of the drops 8 which prevents their coalescence.

The use of gelling agents in a composition 9 may require adjustments at the production plant 2, in particular to ensure a suitable viscosity of the solutions or fluids comprising them, and thus good operation of the plant. Thus, the preparation of a composition according to the invention may comprise heating (between 40° C. and 150° C., in particular between 50° C. and 90° C.) of certain solutions and/or fluids, in particular those comprising at least one gelling agent, or even the various elements, modules and/or devices of the plant and, if appropriate, maintaining this heating until the desired composition 9 is obtained. These technical adjustments fall within the general knowledge of persons skilled in the art.

The aqueous phase of a composition 9 according to the invention comprises water.

In addition to distilled or deionized water, water suitable for the invention may also be natural spring water or floral water.

According to one embodiment, the mass percentage of water of the aqueous phase of a composition 9 according to the invention is at least 40%, preferably at least 50%, more preferably between 70% and 98%, even more preferably between 75% and 95%, relative to the total mass of the continuous phase.

The aqueous phase of a composition 9 according to the invention in the form of a direct emulsion may further comprise at least one base. It may comprise a single base or a mixture of several different bases. The presence of at least one base in the aqueous continuous phase contributes in particular to increasing the viscosity of the latter. According to one embodiment, the base present in the aqueous phase is a mineral base. According to one embodiment, the mineral base is selected from the group consisting of alkali metal hydroxides and alkaline earth metal hydroxides. Preferably, the mineral base is an alkali metal hydroxide, and especially NaOH. According to one embodiment, the base present in the continuous aqueous phase is an organic base. Among the organic bases, mention may be made, for example, of ammonia, pyridine, triethanolamine, aminomethylpropanol, or triethylamine.

A composition 9 according to the invention in the form of a direct emulsion may comprise from 0.01% to 10% by weight, preferably from 0.01% to 5% by weight, and more preferably from 0.02% to 1% by weight relative to the weight of the base, preferably a mineral base, and, in particular, NaOH, relative to the total weight of the composition.

The oily phase and/or the aqueous phase advantageously comprises molecules of cosmetic interest, such as cosmetic active agent(s) and/or additional compounds described below.

According to a first embodiment, in particular when the production device 16 is a microfluidic nozzle 82 or a static mixer, the drops 8 have a mean diameter of between 0.2 µm and 3000 µm, preferably between 20 µm. and 2500 µm, and advantageously between 500 µm and 1500 µm, and/or are monodisperse. Preferably, the drops 8 are macroscopic, i.e. visible to the naked eye, and/or are monodisperse. The monodispersity is obtained, in particular, by implementing a production device 16 chosen from among a nozzle 82. The monodispersity and the measurement protocol relating thereto are described in particular in WO 2012/120043.

According to a second variant embodiment, especially when the production device 16 is a mixer provided with at least one dispersion module, in particular at least one dispersion turbine, the drops 8 have an average diameter of less than 500 µm, or even less than 200 µm. Preferably, the size of the drops is between 0.5 µm to 50 µm, preferably between 1 µm and 20 µm. This variant embodiment makes it possible to dispose of drops of reduced size, especially with respect to drops obtained by a microfluidic process. This small size of drops will have an effect on the texture. In fact, an emulsion according to the invention, formed of finely dispersed drops, offers improved lubricity qualities Preferably, the core 20 is liquid at ambient temperature and atmospheric pressure.

According to a preferred embodiment, the drops 8 comprise a core 20 consisting of at least a first fluid 22 and an envelope forming a shell 24 for retaining and stabilizing the core 20.

Preferably, the shell 24 has a thickness of less than 1000 nanometers, especially between 1 nanometer and 500 nanometers, especially as measured according to the protocol described in WO 2012/120043.

The shell 24 surrounding the drops 8 of the emulsion is stiffened, which has the advantage of conferring superior resistance to the drops 8 and to reducing or preventing coalescence.

Preferably, the shell 24 of the drops 8 is formed of a coacervate layer interposed between the first fluid 22 and the second fluid 26.

The shell 24 is typically formed by coacervation between a first coacervate precursor polymer and a second coacervate precursor polymer. Coacervation is the precipitation of polymers charged with opposite charges.

The shell 24 is formed by coacervation of at least two charged polymers of opposite polarity (or polyelectrolyte), preferably in the presence of a first polymer of the anionic type, and a second polymer, different from the first polymer, of the cationic type.

The coacervation takes place in the presence of a first polymer of the anionic type and a second polymer of the cationic type, which act as stiffening agents of the membrane.

The formation of the coacervate between these two polymers may be caused by a modification of the conditions of the reaction medium (temperature, pH, concentration of reagents, etc.). The coacervation reaction results from the neutralization of these two charged polymers of opposite polarities and allows the formation of a membrane structure by electrostatic interactions between the first and the second polymer. The membrane thus formed around each drop 8 completely encapsulates the core 20 and isolates the first fluid from the second fluid.

The first polymer is initially contained in either the first phase and the second phase, wherein the second polymer is initially contained in the other first phase and second phase before the formation of the drops 8. Thus, a plant 2 according to the invention is so designed that the first polymer is initially contained in the first fluid 22, while the second polymer is initially contained in the second fluid 26 before the formation of the drops 8, or vice versa. Both polymers then migrate to the interface during the formation of the drops 8 where they form the shell by coacervation.

Thus, in the case where the composition according to the invention is in the form of a direct emulsion, before the formation of the drops 8, the anionic polymer is initially contained in the second aqueous fluid 26, while the cationic polymer is initially contained in the first oily fluid 22.

Likewise, in the case where the composition according to the invention is in the form of an inverse emulsion before the formation of the drops 8, the anionic polymer is initially contained in the first aqueous fluid 22, while the cationic polymer is initially contained in the second oily fluid 26.

In the context of the present description, the term "anionic polymer" means a polymer having anionic type chemical functions. We may also speak of anionic polyelectrolyte.

By "anionic chemical function" is meant an AH chemical function capable of giving a proton to give a function A⁻. Depending on the conditions of the medium in which it is found, the anionic type polymer therefore has chemical functions in the AH form, or in the form of its conjugate base A⁻.

As an example of chemical functions of the anionic type, mention may be made of the carboxylic acid functions —COOH, optionally present in the form of a carboxylate anion —COO—.

Preferably, the anionic polymer is hydrophilic or water-soluble in water.

As an example of the anionic type polymer, may be mentioned any polymer formed by the polymerization of monomers at least a portion of which carries anionic type chemical functions, such as carboxylic acid functions. Such monomers are, for example, acrylic acid, maleic acid, or any ethylenically unsaturated monomer containing at least one carboxylic acid function. Among examples of anionic polymers suitable for carrying out the invention, may be mentioned copolymers of acrylic acid or maleic acid and other monomers, such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxypolyethylene glycol methacrylates, hydroxyester acrylates, crosspolymer acrylates and mixtures thereof.

According to one embodiment, the anionic polymer according to the invention is a crosslinked carbomer or copolymer acrylates/$C_{10\text{-}30}$ alkyl acrylate. Preferably, the anionic polymer according to the invention is a carbomer.

According to one embodiment, the shell of the drops comprises at least one anionic polymer, such as, for example, a carbomer.

In the context of the invention, and unless otherwise stated, the term "carbomer" means an optionally crosslinked homopolymer resulting from the polymerization of acrylic acid. It is therefore a poly(acrylic acid) that is optionally crosslinked.

Among the carbomers of the invention, mention may be made of those sold under the names Tego® Carbomer 340FD from Evonik, Carbopol® 981 from Lubrizol, Carbopol ETD 2050 from Lubrizol, or Carbopol Ultrez 10 from Lubrizol.

According to one embodiment, the term "carbomer" or "Carbopol®" means a high molecular weight acrylic acid polymer crosslinked with allyl sucrose or pentaerythritol allyl ethers (handbook of Pharmaceutical Excipients, 5th Edition, pIII). Examples include Carbopol® 910, Carbopol® 934, Carbopol® 934P, Carbopol® 940, Carbopol® 941, Carbopol® 71G, Carbopol® 980, Carbopol® 971P or Carbopol® 974P. According to one embodiment, the viscosity of the carbomer is between 4,000 and 60,000 cP at 0.5% w/w.

The carbomers have other names: polyacrylic acids, carboxyvinyl polymers or carboxy polyethylenes.

A composition according to the invention may comprise from 0.01% to 5%, preferably from 0.05% to 2%, and more preferably from 0.10% to 0.5%, by weight of anionic polymer(s), especially carbomer(s), relative to the total weight of the composition.

In the context of the present description, the term "cationic polymer" means a polymer having chemical functions of the cationic type. We may also speak of cationic polyelectrolyte.

By "chemical function of the cationic type" is meant a chemical function B capable of capturing a proton to give a function $BH^+$. Depending on the conditions of the medium in which it is located, the cationic type polymer therefore has chemical functions in B form, or in $BH^+$ form, its conjugated acid.

Preferably, the cationic type polymer is lipophilic or fat-soluble.

As an example of chemical functions of the cationic type, mention may be made of the primary, secondary and tertiary amine functions, optionally present in the form of ammonium cations.

As an example of a cationic type polymer, may be mentioned any polymer formed by the polymerization of monomers, at least a portion of which carries chemical functions of the cationic type, such as primary, secondary or tertiary amine functions.

Such monomers are, for example, aziridine, or any ethylenically unsaturated monomer containing at least one primary, secondary or tertiary amine function.

Examples of cationic polymers suitable for the implementation of the invention include amodimethicone, derived from a silicone polymer (polydimethylsiloxane, also called dimethicone), modified by primary amine and secondary amine functions.

Mention may also be made of amodimethicone derivatives, for example copolymers of amodimethicone, aminopropyl dimethicone, and more generally linear or branched silicone polymers containing amine functions.

Mention may be made of PEG-14/amodimethicone bis-isobutyl copolymer, Bis ($C_{13\text{-}15}$ Alkoxy) PG-Amodimethicone, Bis-Cetearyl Amodimethicone and bis-hydroxy/methoxy amodimethicone.

Mention may also be made of polysaccharide polymers comprising amine functions, such as chitosan or guar gum derivatives (hydroxypropyltrimonium guar chloride).

Mention may also be made of polypeptide-type polymers comprising amine functions, such as polylysine.

Mention may also be made of polyethyleneimine polymers comprising amine functions, such as linear or branched polyethyleneimine.

According to one embodiment, the drops, and, in particular, the shell of the drops, comprise a cationic polymer which is a silicone polymer modified with a primary, secondary or tertiary amine function, such as amodimethicone.

According to one embodiment, the drops, and, in particular, the shell of the drops, comprise amodimethicone.

According to a particularly preferred embodiment, the cationic polymer has the following formula:

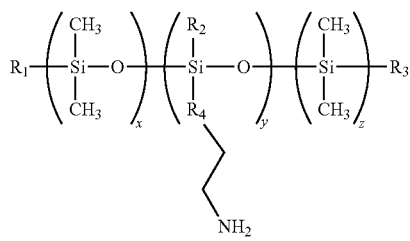

in which:
$R_1$, $R_2$ and $R_3$, independently of each other, represent OH or CH3;
$R_4$ represents a group —CH2- or a group —X—NH— in which X is a divalent alkylene radical C3 or C4;
x is an integer between 10 and 5000, preferably between 30 and 1000, and more preferably between 80 and 300;
y is an integer between 2 and 1000, preferably between 4 and 100, and more preferably between 5 and 20; and
z is an integer between 0 and 10, preferably between 0 and 1, and more preferably equal to 1.

In the aforementioned formula, when $R_4$ is —X—NH—, X is attached to the silicon atom.

In the aforementioned formula, $R_1$, $R_2$ and $R_3$ are preferably $CH_3$.

In the aforementioned formula, $R_4$ is preferably a group —$(CH_2)_3$—NH—.

According to the invention, a composition according to the invention may comprise from 0.01% to 5%, preferably from 0.05% to 2%, and more preferably from 0.10% to 0.5%, by weight of cationic polymer(s), especially amodimethicone(s), relative to the total weight of the composition.

According to an alternative embodiment in which the cationic polymer(s) is/are present in a dispersed oily phase, each drop may comprise from 0.01% to 10%, preferably from 0.05% to 5%, by weight of cationic polymer(s), in particular amodimethicone(s), relative to the total weight of the fatty phase.

The drops 8 are formed according to the drop forming method 8 described in the application WO 2012/120043. The drops 8 thus formed are advantageously monodisperse.

According to an alternative embodiment where the production device 16 is selected from a microfluidic nozzle 82, and the composition 9 contains drops comprising a core surrounded by a shell, an intermediate fluid 21 may be required. The intermediate fluid 21 is then intended to temporarily form a film around the drop formed in the second fluid 26 in order to delay the diffusion of the precursor polymer coacervate present in the first fluid 22, to the interface with the second fluid 26 until the intermediate fluid 21 is mixed with one of the first or second fluids (22 or 26), preferably with the first fluid 22. The intermediate fluid 21 may therefore be an aqueous phase or an oily phase, especially like that defined above but devoid of the anionic and cationic polymer required for the coacervation reaction described above. This variant embodiment is described, in particular, in application WO 2012/120043.

According to this variant embodiment, it is possible to dispense with the intermediate fluid 21 subject to implementing in the oily phase, in particular the dispersed oily phase, a sufficient quantity of gelling agent as described above. This aspect is within the general expertise of persons skilled in the art and is described in more detail in FR1558850 whose content is incorporated by reference.

The composition 9 may be:
a direct emulsion, preferably in which the first fluid is lipophilic and optionally comprises at least one first coacervate precursor polymer, while the second fluid is hydrophilic and optionally comprises at least one second coacervate precursor polymer, or
an inverse emulsion, preferably in which the first fluid 22 is hydrophilic and optionally comprises at least one second precursor polymer of the coacervate, while the second fluid 26 is lipophilic and, optionally, comprises at least one first precursor polymer of the coacervate.

According to a particular variant embodiment, the external fluid 26, especially when represented by an aqueous continuous phase, may also be a direct emulsion. Such a variant embodiment is described in particular in the application FR1651172 whose content is incorporated by reference.

Preferably, the composition 9 does not comprise a surfactant.

With reference to FIG. 1, the storage module 10 is intended to store various solutions making it possible to form the first fluid 22, the second fluid 26 and the intermediate fluid 21.

The storage module 10 comprises a first solution storage assembly 30 comprising the first fluid 22, a second solution storage assembly 32 comprising the second fluid 26, and, optionally, a third solution storage assembly 34 comprising the intermediate fluid 21.

The first storage assembly 30 comprises a tank 36 for storing a first stock solution A and at least one storage tank 38 for storing a first solution of active agents and/or additional compound(s) $A_x$. In the example illustrated in FIG. 1, the first storage assembly comprises three storage tanks 38 for storing first solutions of active substances and/or additional compound(s) $A_1$, $A_2$, $A_3$. Alternatively, the number of storage tanks of the first solutions of active and/or additional compound(s) $A_1$, $A_2$, $A_3$ is strictly less than or strictly greater than three.

The first stock solution A may comprise a first fluid base and, optionally, at least one first precursor polymer of the coacervate of the drops 8.

The first solutions of active and/or additional compound(s) $A_1$, $A_2$, $A_3$ are advantageously different from each other.

Preferably, the first active solutions and/or additional compounds $A_1$, $A_2$, $A_3$ are lipophilic. Preferably, the first active solutions and/or additional compounds $A_1$, $A_2$, $A_3$ are hydrophilic.

The second storage assembly 32 comprises a storage tank 40 of a second stock solution B and at least one storage tank 42 of a second solution of active agent(s) and/or additional compound(s) $B_y$. In the example illustrated in FIG. 1, the second storage assembly 32 comprises three storage tanks 42 of second solutions of active agent(s) and/or additional compound(s) $B_1$, $B_2$, $B_3$. As a variant, the number of storage tanks for second solutions of active substances and/or additional compound(s) $B_1$, $B_2$, $B_3$ is strictly less than or strictly greater than three.

The second stock solution B may comprise a second fluid base and, optionally, at least one second coacervate precursor polymer of the drops 8.

The second solutions of active agent(s) and/or additional compound(s) $B_1$, $B_2$, $B_3$ are advantageously different from each other.

Preferably, the second solutions of active agent(s) and/or additional compounds $B_1$, $B_2$, $B_3$ are lipophilic. Preferably, the second active solutions and/or additional compounds $B_1$, $B_2$, $B_3$ are hydrophilic.

Advantageously, when the first solutions of active agent(s) and/or additional compounds $A_1$, $A_2$, $A_3$ are lipophilic, the second active solutions and/or additional compounds $B_1$, $B_2$, $B_3$, $B_4$ are hydrophilic, and vice versa.

Optionally, the storage module 10 comprises at least one storage tank 44 of a perfume or perfume concentrate solution $P_w$. In the example illustrated in FIG. 1, the storage module 10 comprises three storage tanks 44 of perfume concentrate solutions $P_1$, $P_2$, $P_3$. As a variant, the number of storage tanks 44 of perfume concentrate solutions $P_1$, $P_2$, $P_3$ is strictly less than, or strictly greater than, three.

Solutions of perfume concentrates $P_w$ advantageously have different compositions from each other.

Solutions of perfume concentrates $P_w$ are, for example, perfuming agents. Among perfuming agents, mention may be made of any type of perfume or fragrance, wherein these terms are used here interchangeably. These perfumes or fragrances are well known to persons skilled in the art and include, in particular, those mentioned, for example, in S. Arctander, Perfume and Flavor Chemicals (Montclair, N.J., 1969), S. Arctander, Perfume and Flavor Materials of Natural Origin (Elizabeth, N.J., 1960) and in "Flavor and Fragrance Materials," 1991 (Allured Publishing Co. Wheaton, Ill., USA). The perfumes used may include natural products such as extracts, essential oils, absolutes, resinoids, resins, concretes, etc., as well as basic synthetic substances such as hydrocarbons, alcohols, aldehydes and ketones, ethers, acids, esters, acetals, ketals, nitriles, etc., including saturated and unsaturated compounds, aliphatic, alicyclic and heterocyclic compounds.

The third storage unit 34 comprises a storage tank 50 of a third stock solution C and at least one storage tank 51 of a third solution of active agent(s) and/or additional compound(s) $C_z$, The third stock solution C contains or is formed of the first stock solution A or the second stock solution B, but is devoid of coacervate precursor polymer.

The first solutions of active agent(s) and/or additional compounds $A_x$ (in particular $A_1$, $A_2$, $A_3$), By, (in particular $B_1$, $B_2$, $B_3$) and $C_z$, (in particular $C_1$), contain, for example, the same fluid base as, respectively, the first stock solution A, the second stock solution B, and the third stock solution C, and incorporate, in addition, one or more molecules of interest, in particular of cosmetic interest.

In particular, the active agent(s) $A_x$ (in particular $A_1$, $A_2$, $A_3$), $B_y$, (in particular $B_1$, $B_2$, $B_3$) and $C_z$, (in particular $C_1$) are, for example, chosen from moisturizing agents, cicatrizing agents, depigmenting agents, UV filters, desquamating agents, antioxidants, active agent(s) stimulating the synthesis of dermal and/or epidermal macromoleculars, dermody-contracting agents, antiperspirants, soothing agents and/or anti-inflammatory agents, anti-age agents, and their mixtures.

In particular, the additional compounds $A_x$ (in particular $A_1$, $A_2$, $A_3$), $B_y$, (in particular $B_1$, $B_2$, $B_3$) and $C_z$, (in particular $C_1$) are, for example, chosen from texturing agents(s) (different from the cationic and anionic polymers forming the shell 24 by coacervation), powders, flakes, coloring agents, especially chosen from organic or inorganic coloring agents, optical effect materials, liquid crystals, preservatives, humectants, stabilizers, chelators, emollients, and mixtures thereof.

According to a particular embodiment, at least one of the active agent(s) $A_x$ and at least one of the agents $B_y$ is a cationic or anionic polymer forming the shell 24 by coacervation, in which case the stock solutions A and B are devoid of the cationic and anionic polymers intended to form the shell 24 by coacervation.

Of course, persons skilled in the art will take care to choose the additional active agent(s) and/or compound(s) and/or their quantities according to the aqueous or oily nature of the stock solution in question and/or in such a way that the advantageous properties of a composition 9 according to the invention and, in particular, the integrity of the drops 8 are not, or not substantially, impaired by the intended addition. These adjustments are within the expertise of persons skilled in the art. In this respect, the control unit 14 is preferably parameterized accordingly, and, in particular, in order to prevent any mixing or bringing into contact of solutions that are not, or not very, miscible with one another, and/or raw materials that are not very, or not t all, compatible with one another.

Each tank 36, 38, 40, 42, 44, 50, 51 of the storage module 10 is removable, i.e. it may be removed from the storage module 10 and possibly replaced by another storage tank.

The volume of the storage tanks 36, 38, 40, 42, 44, 50, 51 of the storage module 10 is generally less than 10 L.

The preparation module 12 is connected to the storage module 10.

The preparation module 12 is designed to prepare the first fluid 22, the second fluid 26, and the intermediate fluid 21.

In particular, the preparation module 12 is able to form the first fluid 22 by mixing determined quantities of the first stock solution A and determined quantities of one or more first solutions of active agent(s) and/or additional compound(s) $A_x$.

The preparation module 12 is also capable of forming the second fluid 26 by mixing determined quantities of the second stock solution B, determined quantities of one or more second solutions of active agent(s), and/or additional compound(s) $B_y$.

If necessary, the preparation module 12 is suitable for preparing the intermediate fluid 21 by mixing determined quantities of the third stock solution C and, optionally, determined quantities of at least the third solution of active agent(s), and/or additional compound(s) $C_z$.

In a variant, the preparation module 12 is also able to add a specific quantity of one or more perfume or perfume concentrate solution(s) $P_w$, in the first fluid 22 and/or in the second fluid 26 and/or optionally in the intermediate fluid 21, preferably in the first fluid 22.

The preparation module 12 is furthermore designed to convey the first fluid 22, the second fluid 26 and, if appropriate, the intermediate fluid 21, to the device 16 for producing drops 8.

When the storage module 10 comprises several tanks 38 containing several first solutions of active agent(s) and/or additional compound(s) $A_x$, and/or several tanks 42 containing several second solutions of active agent(s) and/or compound(s) $B_y$, and optionally several tanks 51 containing several third solutions of active agent(s) and/or additional compound(s) $C_z$, and/or several tanks 44 containing several solutions of perfume(s) $P_w$, the preparation module 12 is suitable for selectively mixing:

- a determined quantity of one or more first solutions of active agent(s) and/or additional compound(s) $A_x$ with a determined quantity of the first stock solution A to form the first fluid 22,
- a determined quantity of one or more second solutions of active agent(s) and/or additional compound(s) $B_y$, with a determined quantity of the second stock solution B to form the second fluid 26,
- optionally, mixing a determined quantity of one or more third solutions of active agent(s) and/or additional compound(s) $C_z$ with a determined quantity of third stock solution C to form the intermediate fluid 21, and
- optionally, mixing a determined quantity of one or more perfume solutions $P_w$ (or perfume concentrate solutions $P_w$) with the determined quantity of the first stock solution A and/or the second stock solution B and/or the third stock solution C, preferably the first stock solution A.

The preparation module 12 comprises ducts 60 for conveying solutions from the tanks of the storage module 10, the selection valves 62, a pumping system 64 and mixers 66.

The feed path ducts 60 are designed to convey the solutions from the tanks of the storage module 10 to the pumping system 64.

The selection valves 62 are disposed at the outlet of each storage tank 36 of the first stock solution A, of each tank 38 for storing the first active solutions and/or the additional compound(s) Ax, of each tank 40 for storing the second stock solution A, of each tank 42 for storing the second solutions of active agent(s) and/or additional compound(s) $B_y$, each storage tank 50 of the third stock solution C, each tank 51 for storing the third solutions of active agent(s) and/or additional compound(s) $C_z$, and each tank 44 for storing the perfume solutions(s) $P_w$. Thus, for each tank 36, 38, 40, 42, 44, 50, 51, the preparation module 12 comprises a corresponding selection valve 62.

The selection valves 62 make it possible to selectively open or close the corresponding tank 36, 38, 40, 42, 44, 50, 51. The selection valves 62 thus make it possible to stop or modify the solution flow from the tanks 36, 38, 40, 42, 44, 50, 51.

The selection valves 62 are connected to the corresponding tanks 36, 38, 40, 42, 44, 50, 51 via the fluid feed ducts 60.

In the embodiment illustrated in FIG. 1, the outlets of all the selection valves 62 corresponding to the tanks 38 for storing first solutions of active agent(s) and/or additional compound(s) $A_1, A_2, A_3$ are joined to form a single duct 60A for conveying first solutions of active agent(s) and/or additional compound(s) $A_1, A_2, A_3$ to the pumping system 64. Similarly, the outputs of the assembly selection valves 62 corresponding to the tanks 42 for storing second solutions of active agent(s) and/or additional compound(s) $B_1, B_2, B_3$ are joined to form a single duct 60B for conveying second solutions of active agent(s) and/or additional compound(s) $B_1, B_2, B_3$ to the pumping system 64. Similarly, the outputs of all the selection valves 62 corresponding to the tanks 44 for storing perfume solutions $P_1, P_2, P_3$ are joined to form a single duct 60P for conveying perfume solutions $P_1, P_2, P_3$ to the pumping system 64.

The control unit 14 is designed to control the activation of the selection valves 62 and to control the pumping device 64. For this, the control unit 14 is connected to the selection valves 62 and to the pumping system 64. Only a portion of the connections is illustrated in FIG. 1.

The control unit 14 is designed to determine the quantity of one or more first solutions of active agents and/or additional compound(s) $A_x$, possibly of one or more perfume solutions $P_w$, to mix with a determined quantity of the first stock solution A in order to obtain the first fluid 22. Similarly, the control unit 14 is designed to determine the quantity of one or more second solutions of active agent(s) and/or additional compound(s) $B_y$, and optionally one or more perfume solutions $P_w$, to be mixed with a predetermined quantity of the second stock solution B in order to obtain the second fluid 26. The control unit 14 is, in addition and if necessary, designed to determine the quantity of the third stock solution C to be mixed with a determined quantity of one or more third solutions of the active agent(s) and/or additional compound(s) $C_z$, and any of one or more of the perfume solutions $P_w$, to obtain the intermediate fluid 21.

The control unit 14 is, for example, a computer.

The pumping system 64 is designed to pump fluid from each fluid delivery duct 60, 60A, 60B, 60P. The pumping system 64 thus makes it possible to regulate the flow of fluids by suction or discharge of fluids.

The pumping system 64 comprises a first pump 68 for pumping fluids from the first storage module 30 and possibly the storage module comprising the tank(s) 44, a second pump 70 for pumping fluids from the second storage module 32 and possibly the storage module comprising the tank(s) 44, and a third pump 72 for pumping fluids from the third storage module 34 and possibly the storage module comprising the tank(s) 44.

The first pump 68 is designed to selectively pump the fluids from the duct 60, connected to the tank 36 for storing the first stock solution A, the duct 60A, and possibly the duct 60P. The output of the first pump 68 is connected to a mixer 66.

The second pump 70 is designed to selectively pump the fluids from the duct 60, connected to the tank 40 for storing the second stock solution B, the duct 60B, and possibly the duct 60P. The output of the second pump 70 is connected to a mixer 66.

The third pump 72 is designed to selectively pump the fluids from the duct 60, connected to the storage tank 50 of the third stock solution C, of the duct 60 connected to the tank 51 for storing third solutions of active agents and/or additional compound(s) $C_z$, and possibly the duct 60P. The output of the third pump 72 is connected to a mixer 66.

The pumps 68, 70, 72 are, for example, vacuum pumps, piston pumps or even peristaltic pumps.

The mixers 66 are designed to homogenize the fluid mixtures from the pumping system 64. In the embodiment illustrated in FIG. 1, the plant 2 comprises three mixers 66, wherein one of the mixers 66 is connected to the first pump 68, the second mixer 66 is connected to the second pump 70, and the third mixer is connected to the third pump 72. The mixer 66 connected to the first pump 68 is able to mix the first stock solution A with the first solutions of active agent(s) and/or additional compound(s) $A_1, A_2, A_3$ and/or the perfume solutions $P_1, P_2, P_3$ to obtain the first fluid 22. The mixer 66 connected to the second pump 70 is able to mix the second stock solution B with the second solutions of active agent(s) and/or additional compound(s) $B_1, B_2, B_3$ and/or the perfume solutions $P_1, P_2, P_3$ thus making it possible to obtain the second fluid 26. The mixer 66 connected to the third pump 72 is able to mix the third stock solution C with the third solution of active agent(s) and/or additional compound(s) $C_1$ and/or the perfume solutions $P_1$, $P_2$, $P_3$ to obtain the intermediate fluid 21.

The mixers 66 are, for example, static mixers.

The outputs of the mixers 66 are each connected to the device 16 for producing the composition 9 via fluid feed ducts.

The production device 16 may comprise at least one element chosen from among:
- a nozzle 82 as described below,
- a mixer provided with at least one dispersion module, in particular at least one dispersion turbine (or deflocculating turbine), and
- a static mixer.

According to a first variant, the production device (16) comprises at least one element chosen from a microfluidic nozzle 82, in particular as described in WO2012120043 or WO2015055839 whose contents are incorporated by reference. This variant is advantageous in that it makes it possible to produce compositions 9 comprising macroscopic and monodisperse drops, which, moreover, have a particularly interesting changing texture.

With a microfluidic nozzle 82, the various fluids used form a multi-component drop, according to a hydrodynamic mode known as "dripping" or "jetting" (formation of a liquid jet at the outlet of the microfluidic device, then fragmentation of the jet into the ambient air under the effect of gravity). Preferably, the flow rates of the various fluids required to obtain a composition according to the invention are adjusted for a flow at the outlet of the microfluidic device drop by drop (or "dripping").

According to a second variant, the production device (16) comprises at least one element chosen from a mixer provided with at least one dispersion module, in particular at least one dispersion turbine (or deflocculating turbine). This variant is advantageous in that it makes it possible to produce compositions 9 with a high production yield and having a particularly interesting changing texture.

According to a third variant, the production device (16) comprises at least one element chosen from a static mixer, for example like the static mixer 66. Advantageously, the static mixer may be a microfluidic device comprising a channel capable of forming relatively monodisperse drops, in particular a device comprising a microfluidic channel comprising a two-dimensional network of obstructions, arranged in a plurality of rows of regularly spaced obstacles, wherein the rows of obstacles are arranged orthogonal to the direction of flow of the fluid(s) through the microfluidic channel, and wherein at least some of the rows of obstacles are offset from an adjacent row of obstacles. Preferably, the device is as described in WO2014138154 whose content is incorporated by reference.

According to a fourth variant, the production device (16) comprises at least one element chosen from among a microfluidic nozzle 82, and then a mixer provided with at least one dispersion module, in particular at least one dispersion turbine (or deflocculating turbine).

According to a fifth variant, the production device (16) comprises at least one element selected from among a microfluidic nozzle 82 and a static mixer.

Referring to FIG. 1, the production device 16 comprises at least one fluid distribution module 80 and at least one nozzle 82 to form a composition 9 comprising drops 8, as shown in detail in FIG. 2. The production device 16 preferably comprises a plurality of fluid distribution modules 80 arranged parallel to each other and a plurality of identical nozzles 82 arranged parallel to each other. Advantageously, each distribution module 80 is connected to a multitude of nozzles 82.

Each nozzle 82 is thus connected upstream to a fluid distribution module 80. Each fluid intended for the production of a composition 9 comprising drops 8, flows into the dispensing module 80, then into the nozzle 82 to form the composition.

Referring to FIG. 1, each distribution module 80 comprises at least a first rail 86 of the first fluid 22, a second rail 88 of the second fluid distribution 26, and a third rail 90 of the intermediate fluid 21. Each module dispenser 80 further comprises first, second and third connections connecting the nozzle 82 respectively to the first, second and third distribution rails 86, 88, 90. The first distribution rail 86 is connected to the duct for conveying the first fluid 22. The second distribution rail 88 is connected to the duct for conveying the second fluid 26. The third distribution rail 90 is connected to the duct for conveying the intermediate fluid 21.

In a variant, each distribution module 80 has only the first distribution rail 86 of the first fluid 22, and the second distribution rail 88 of the second fluid 26. In addition, in this variant, each distribution module 80 comprises only the first and second connections connecting the nozzle 82 respectively to the first and second rails 86, 88.

The distribution modules 80 are advantageously made of a composite material, for example, by stereolithography.

Alternatively, the distribution modules 80 may be made of a metallic material, for example stainless steel. Alternatively, the distribution modules 80 may be made of polymer material.

As the first rail 86, the second rail 88, and the third rail 90 are substantially identical, only the first rail 86 is described in the following.

The first rail 86 comprises an inlet orifice 100 through which the first fluid 22 is introduced, and an outlet orifice 102 allowing the introduction of the first fluid 22 into the nozzle 82. The inlet orifice 100 is connected to the preparation 12.

As the first, second and third connections are substantially identical, only the first connections are described below.

Each first connection is for connecting one of the outlets 102 of the first rail 86 to one of the formation nozzles 82.

Each first connection is designed to advantageously create a pressure drop 83. The first connection comprises, for example, a regular pressure drop over the entire length of the pressure drop, formed for example by a helical duct.

Alternatively, the first connection comprises a regular pressure drop, such as a groove in a plate.

Alternatively, each first connection comprises a regular pressure drop such as a flexible or rigid rectilinear tube.

In a variant, each first connection comprises a so-called "exceptional" pressure drop, i.e. a sudden change in the fluid passage section, such as a perforated plate of holes having a very small cross-section relative to at the section of the tubular collector.

Thanks to the pressure drop produced, it is possible to regulate the flow of fluid downstream of the pressure drop and to homogenize the fluid injected between the nozzles 82.

The formation nozzle 82, shown in detail in FIG. 2, is particularly suitable for the production of drops 8 as described above.

The nozzle 82 comprises a hollow body 175 delimiting an internal duct 176 and an external duct 178. The internal duct 176 and the external duct 178 extend along a longitudinal axis AA' that is vertical in FIG. 2, and are arranged coaxially along the longitudinal axis AA'.

The external duct 178 opens downwards through an opening 188 for forming the drops 8.

The formation nozzle 82 further comprises an external feed path 193 of the first fluid 22, an external feed path 180 of the second fluid 26, and, optionally, an external feed path 182 of the intermediate fluid 21. The external feed path 193, and optionally 182, of the formation nozzle 82 is/are connected to the internal duct 176. The external feed path 180 of the forming nozzle 82 is connected to the external duct 178.

Thus, the first fluid 22 flows through the internal duct 176, while the second fluid 26 flows from the external feed duct 180 to the external duct 178. The intermediate fluid 21 flows from the external feed duct 182 into the internal duct 176.

The hollow body 175 is advantageously made of composite material or polymer. This material is for example a thermosetting resin of the epoxy type. Examples of resins are marketed by the company 3D Systems under the references "accura extreme" or "accura 60".

The inner duct 176 is formed by an internal tube 190. The internal tube 190 defines internally an internal volume 192 for circulating the first fluid 22 connected upstream to one of the first connections as described above.

The internal volume 192 of the internal tube 190 opens upstream through an upstream access 193 connected to a first connection. Optionally, the internal volume 192 of the internal tube 190 opens downstream through a downstream access 180 connected to a third connection.

The external duct 178 is formed by an external tube 196. The external tube 196 is connected upstream to one of the second connections as described above.

The formation nozzle 82 further comprises at least one metal tube 224 extending along the longitudinal axis AA'.

In the example shown in FIG. 2, the formation nozzle 82 comprises a metal tube 224 disposed in the internal volume 192 of the internal duct 176 and protruding axially at the connection between the intermediate feed path 182 and the internal duct 176.

The metal tube 224 has a cross-section that is advantageously circular and substantially less than the cross-section of the internal duct 176.

Thus, the intermediate fluid 21 is able to flow from the intermediate feed path 182 to the inside of the metal tube 224 by overflow after being raised along the metal tube 224.

The metal tube is attached to the body 175 of polymeric material.

The hollow body 175 is advantageously manufactured by stereolithography. Once the hollow body 175 has been manufactured, the metal tubes 224 are attached to the body 175.

The rail 18 is connected to each nozzle 82.

The collector 18 is able to collect the composition 9, and, in particular, the drops 8 produced by the production device 16.

The collector 18 comprises a collection module 280 and a purge valve 282.

The collection module 280 is, for example, a container such as a bottle in which the composition 9 is stored, and, in particular, the drops 8. Such a bottle is advantageously intended directly for use by a user.

The purge valve 282 is able to be activated to convey the composition 9, in particular the drops 8, and the fluids out of the rail 18, advantageously to a purge tank 284. The purge valve 282 is, in particular, used during transitional phases of starting and stopping production in order to clean the plant 2.

According to a particular embodiment, the production device 16 and/or the collector 18, preferably the production device 16, further comprise(s) at least one injection device 200 of a solution D for increasing the viscosity of the second fluid 26. When the second fluid 26 is hydrophilic, the solution for increasing the viscosity preferably comprises a base, preferably sodium hydroxide (NaOH). Thus, according to a particular embodiment in which the composition is a direct emulsion, the production device 16 represented by at least one nozzle 82, may further comprise a distribution rail 91 of the solution for increasing the viscosity connected to each nozzle 82, in order to inject, after the formation of the drops, the solution for increasing viscosity in the second fluid 26.

The operation of the plant 2 for producing a composition 9, in particular a cosmetic composition, comprising drops 8 according to the invention will now be described, with reference to FIGS. 1 and 2.

Initially, depending on the desired composition 9, in particular the drops 8, and, in particular, depending on the color and/or the nature and/or content of active agents and/or texture, the control unit 14 determines a determined quantity of one or more first solutions of active agent(s) and/or additional compound(s) $A_x$ and/or possibly a determined quantity of one or more perfume concentrate solutions $P_w$ to mix with a predetermined quantity of the first stock solution A to form the first fluid 22. The control unit 14 advantageously determines a determined quantity of one or more second solutions of active agents and/or additional compound(s) $B_y$, and/or one or more perfume concentrate solutions $P_w$ to be mixed with a predetermined quantity of the second stock solution B to form the second fluid 26. The control unit 14 determines, also, if appropriate, a determined quantity of one or more third solutions of active agent(s) and/or additional compound(s) $C_z$ and/or one or more perfume concentrate solutions $P_w$ to mix with a determined quantity of the third stock solution C to form the intermediate fluid 21.

The selection valves 62 and the pumping system 64 are then designed accordingly.

Then, each fluid coming from the storage tanks 36, 38, 40, 42, 44, 50 and 51 is selectively conveyed, possibly via the selection valves 62, to the pumping system 64.

Then, the mixers 66 make it possible to mix the fluids coming from the different storage tanks to form the first fluid 22, the second fluid 26, and, where appropriate, the intermediate fluid 21.

Subsequently, the first fluid 22, optionally the intermediate fluid 21, and the second fluid 26 are conveyed, simultaneously or sequentially, from the corresponding mixer 66 to, respectively, the first distribution rail 86, the third rail 90 and the second distribution rail 88. The first fluid 22, the second fluid 26, and the intermediate fluid 21 are then conveyed from the corresponding distribution rails 86, 88, 90 to the nozzles 82 through the pressure loss blocks.

The first fluid 22 flows from the external feed path 193 into the internal volume 192 of the internal duct 176.

The intermediate fluid 21 rises along the metal tube 224 from the intermediate feed path 182 and then enters by overflow into the metal tube 224 disposed in the internal volume 192 of the internal duct 176.

The second fluid 26 flows from the external feed path 180 into the external duct 178.

Then, the first fluid 22 and the intermediate fluid 21 are injected, at the downstream end of the metal tube 224, into the second fluid 26 flowing in the external duct 178 to form the composition 9 comprising a dispersion of drops 8. The composition 9 comprising the dispersion of drops 8 thus formed, then flows out of the production device 16 into the collection module 280 of the collector 18.

Advantageously, the method comprises, subsequently, the cleaning of the plant 2, for example by flowing the first stock solution A, the second stock solution B, and, if necessary, the third intermediate solution C, and therefore without the addition of active agent(s) and/or additional compound and/or perfume, in the preparation module 12 and the production device 16. The purge valve 282 is opened to allow the flow of fluids into the drain pan 284.

Optionally, after the step of forming the composition 9, the method may comprise injecting a solution for increasing the viscosity of the composition 9, in particular the second fluid 26, wherein this step is carried out at the production device 16 and/or the collector 18, preferably the production device 16.

Then, the method comprises the preparation in the same preparation module 12, of at least a first additional fluid of the composition identical to or different from the first fluid and/or at least one second additional fluid of a composition identical to or different from the second fluid and/or, optionally, at least one additional intermediate fluid of a composition identical to or different from the intermediate fluid 21. The composition of the first additional fluid, respectively of the second additional fluid, respectively of the additional intermediate fluid may differ from the first fluid 22, respectively the second fluid 26 or the intermediate fluid 21, in particular by the quantity and/or type of the first and/or additional compounds $A_x$, and/or the perfume concentrate solutions $P_w$ introduced, respectively of the second and/or additional compounds $B_y$, and/or perfume concentrate solutions $P_w$ introduced, respectively the third active agent(s) and/or additional compounds $C_z$ and/or perfume solutions $P_w$ introduced.

Then, the first additional fluid is conveyed into the first distribution rail 86, the second additional fluid is conveyed into the second distribution rail 88 and, if appropriate, the third additional fluid is conveyed into the third distribution rail 90.

Finally, an additional composition comprising additional drops is obtained from the production device 16.

Advantageously, the plant 2 is housed in a common frame so that the storage module 10, the preparation module 12, the control unit 14, the production device 16, and the collector 18 are movable together.

As indicated above, a composition 9 according to the invention may be a cosmetic composition, and, in particular, a composition for the make up and/or care of keratin materials, especially the skin.

The cosmetic compositions according to the invention may be skincare, sun protection, cleaning (make-up removal), hygiene or make-up products for the skin.

These compositions are therefore intended to be applied especially to the skin.

According to one embodiment, the compositions of the invention are in the form of a foundation, a make-up remover, a facial and/or body and/or hair care, anti-age agent, a sunscreen, oily skin care, whitening care, moisturizer, BB cream, a tinted cream or a foundation, a face and/or body cleanser, shower gel or shampoo.

A care composition according to the invention may be, in particular, a solar composition, a care cream, a serum or a deodorant.

The compositions according to the invention may be in various forms, in particular in the form of cream, balm, lotion, serum, gel, gel-cream or mist.

Thus, the present invention also relates to the non-therapeutic cosmetic use of a cosmetic composition obtained by implementing a production plant 2 as described above, especially as make-up, hygiene, cleaning, and or care of keratin materials, especially the skin.

A production plant 2 according to the invention is particularly advantageous in that it allows customization (or personalization) of compositions, in particular cosmetic, in the form of emulsion or dispersion, and in particular obtained by a microfluidic process, directly by the consumer at the point of sale.

Throughout the description, including the claims, the phrase "comprising one" should be understood as being synonymous with "comprising at least one", unless the opposite is specified.

The expressions "comprised between . . . and . . . ", "comprised from . . . to . . . " and "from . . . to . . . " must be understood as being inclusive, unless otherwise specified.

The quantities of the ingredients in the examples are expressed as percentage by weight relative to the total weight of the composition, unless otherwise indicated.

The following examples illustrate the present invention without limiting its scope.

EXAMPLES

Example 1

In this example, a composition 9 according to the invention of a direct emulsion type is manufactured by means of a production plant according to the invention.

The first coacervate precursor polymer is of a cationic and lipophilic type (amodimeticone), and the second coacervate precursor polymer (carbomer) is of an anionic and hydrophilic type.

The first polymer is contained in the oily internal fluid. The second polymer is contained in the aqueous external fluid.

A coacervate is formed at the interface between the polyacrylic acid contained in the external fluid and an aminosilicone (amodiméticone) contained in the internal fluid, after formation of drops 8 in the external fluid.

The meeting of these two polymers causes the coacervation and stiffening of the membrane around the drops 8, while the implementation of an intermediate fluid slows this meeting and thus prevents fouling of the microfluidic nozzles.

The production device 16 comprises a distribution module 80 provided with distribution rails 86, 88 and 90, a plurality of nozzles (82) arranged in parallel with each other, wherein each distribution rail (86, 88, 90) is connected to the corresponding nozzle (82) by a connection forming a pressure drop.

The following flows are applied:

External fluid: 80 mL/hour,

Internal fluid: 15 mL/hour, and

Intermediate fluid: 5 mL/hour.

The composition of each fluid is described in the table below.

| Phase | Commercial references | INCI | % weight |
|---|---|---|---|
| Internal fluid | DUB ININ | Isononyl isononanoate | 99.8% |
| | CAS 3131 de Nusil | Aminosilicone | 0.2% |
| External fluid | Osmosis water | Aqua | sqf* |
| | Tego Carbomer 340FD | Carbomer | 0.5% |
| | Microcare PE | Phenoxyethanol | 0.9% |
| | Microcare Emollient PTG | Pentylene glycol | 2.2% |
| Intermediate fluid | DUB ININ | Isononyl isononanoate | 100% |

*Sufficient quantity for

A direct emulsion is obtained wherein the drops 8 have a diameter of approximately 1 millimeter with a coacervate membrane.

In a variant, the dispersion of drops 8 contains a perfume agent, in particular as described above.

Alternatively, the nozzles 82 are removable and are considered to be consumables.

As a variant, a viscosification module of the external phase is introduced at the nozzle, after the formation of the drops 8.

In a variant, the internal fluid further comprises at least one gelling agent (in particular 15% by weight of Rheopearl KL2 (INCI: Dextrin Palmitate) relative to the weight of the internal fluid, which makes it possible to dispense with the intermediate fluid. For the manufacture of the composition 9, this requires at least heating of the solution and the fluid comprising this gelling agent to a temperature of 80° C.

Thus, the plant 2 according to the invention allows the rapid production of a composition 9, in particular drops 8, because of the presence of several first, second and third distribution rails 86, 88, 90 and several nozzles 82 arranged in parallel with each other. Such parallelism makes it possible to increase the flow rate and the production of the composition 9. Thus, it is possible to produce many more drops 8 in a reduced time.

The plant 2 for producing drops 8 also makes it possible to produce numerous drops 8 having different compositions as a function of the first active agent solutions, second active agent solutions, and solutions of perfume concentrates present in the storage module 10. The selection and control of the flow of each solution contained in the tanks of the storage module 10 may be easily controlled by means of the selection valves 62 and the pumping system 64.

The plant 2 is, furthermore, easy to clean thanks to the purge valve 282 and the flow of the stock solutions in the plant 2. Thus, the cleaning is performed without friction. It is therefore easy and quick to change the composition of the composition 9, in particular of the drops 8.

As the different elements of the plant 2 are directly connected to each other, the plant 2 is optimized to minimize fluid losses (or dead volumes).

In addition, the production plant 2 involves little mechanical risk since the mixers 66 are static mixers and do not have moving parts. Finally, the plant 2 is silent and operates at ambient temperature, so it is may be easily installed in points of sale.

The plant 2 thus allows the production of the compositions, in particular cosmetics, directly at points of sale, for example. In this case, a user is able to perform a composition selection among a plurality of predefined selected compositions, in particular with regard to their expectations in terms of colors, active agent(s) and/or texture, wherein the composition selection is transmitted to the control unit 14. The plant 2 operates autonomously and may be configured according to the needs of a user.

Example 2: Anti-Aging Serum

In this example, a composition 9 according to the invention of the direct emulsion type is manufactured by means of a production plant according to the invention and the protocol described in Example 1.

| Phase | Commercial references | INCI | % weight |
|---|---|---|---|
| Internal fluid | DUB ININ | Isononyl Isononanoate | Sqf* |
| | KF-96A-50CS (PDMS 50 cSt) | Dimethicone | 44.68 |
| | Ionol CP | BHT (butylated hydroxytoluene) | 0.45 |
| | D&C Red No17 K7007 | CI 26100 | 0.0013 |
| | Nusil CAS 3131 | Amodimethicone | 0.18 |
| External fluid | Osmosis water | Water | Sqf* |
| | Microcare PE | Phenoxyethanol | 0.88 |
| | Microcare Emollient PTG | Pentylene glycol | 2.20 |
| | Tego Carbomer 340FD | Carbomer | 0.27 |
| | Rhodicare T | Xanthan gum | 0.11 |
| | Phylcare Sodio Yaluronato XS | Sodium hyaluronate | 0.01 |
| | Glycerine codex (99%) | Glycerine | 4.40 |
| | Zemea | Propanediol | 5.50 |
| | EDETA BD | Disodium EDTA | 0.03 |
| | Solution 10% Sodium Hydroxide Pellets PRS codex | Water; sodium hydroxide | 0.04 |
| Intermediate fluid | DUB ININ | Isononyl isononanoate | 100 |

*Sufficient quantity for

The anti-aging serum with the following ingredients has been prepared.

| Name | INCI name | % w/w PHASES | % w/w |
|---|---|---|---|
| AQUEOUS GEL PHASE | | | |
| Osmosis water | Water | 86.56 | 78.70 |
| Microcare PE | Phenoxyethanol | 0.88 | 0.80 |
| Microcare Emollient PTG | Pentylene glycol | 2.20 | 2.00 |
| Tego Carbomer 340FD | Carbomer | 0.27 | 0.25 |
| Rhodicare T | Xanthan gum | 0.11 | 0.10 |
| Phylcare Sodio Yaluronato XS | Sodium hyaluronate | 0.01 | 0.010 |
| Glycerine codex (99%) | Glycerine | 4.40 | 4.00 |
| Zemea | Propanediol | 5.50 | 5.00 |
| EDETA BD | Disodium EDTA | 0.03 | 0.030 |
| Solution 10% Sodium Hydroxide Pellets PRS codex | Water; sodium hydroxide | 0.04 | 0.038 |
| Total | | 100.00 | 90.93 |
| FATTY PHASE | | | |
| DUB ININ | Isononyl Isononanoate | 54.68 | 4.96 |
| KF-96A-50CS (PDMS 50 cSt) | Dimethicone | 44.68 | 4.06 |

-continued

| Name | INCI name | % w/w PHASES | % w/w |
|---|---|---|---|
| Ionol CP | BHT (butylated hydroxytoluene) | 0.45 | 0.040 |
| D&C Red No17 K7007 | CI 26100 | 0.0013 | 0.00012 |
| Nusil CAS 3131 | Amodimethicone | 0.18 | 0.020 |
| | Total | 100.00 | 9.08 |
| | Total | | 100.00 |

The final composition 9 comprises translucent pink oily phase drops dispersed in a colorless aqueous gel.

The invention claimed is:

1. A plant for producing a composition, comprising drops of at least one first fluid dispersed in a second fluid that is substantially immiscible with the first fluid, wherein each drop comprises a core formed of the first fluid, wherein the plant comprises:
    a device for producing the composition,
    a storage module comprising:
        at least one storage tank of at least a first stock solution, and at least one storage tank of at least a first solution of active agent(s) and/or additional compound(s), and
        at least one storage tank of at least one second stock solution
    a preparation module, connected to the storage module, designed to prepare at least:
        the first fluid by mixing determined quantities of the first stock solution and at least the first solution of active agent(s) and/or additional compound(s), and
        the second fluid by mixing determined quantities of the second stock solution,
        wherein the preparation module is suitable for conveying in both a simultaneous manner and a sequential manner the first fluid and the second fluid in the production device,
    a control unit designed to:
        determine the quantity of one or more first solutions of active agents and/or additional compound(s) to be mixed with a determined quantity of the first stock solution to obtain the first fluid.

2. The plant according to claim 1, wherein the storage module further comprises at least one storage tank of at least one perfume solution, wherein the preparation module is designed to add a determined quantity of the perfume solution(s), in the first fluid and/or in the second fluid and/or in the intermediate fluid.

3. The plant according to claim 1, wherein the storage module comprises several tanks containing several first solutions of active agent(s) and/or additional compound(s), and/or several tanks containing several second solutions of active agent(s) and/or additional compound(s),
    wherein the preparation module is able to mix selectively:
        a determined quantity of one or more first solutions of active agent(s) and/or of additional compound(s) with a determined quantity of the first stock solution,
        a determined quantity of one or more second solutions of active agent(s) and/or of additional compound(s) with a determined quantity of the second stock solution.

4. The plant according to claim 1, wherein each storage tank of the storage module is removable.

5. The plant according to claim 1, wherein the preparation module comprises selection valves of each solution to be mixed to obtain at least the first fluid, the second fluid, and, if appropriate, the intermediate fluid.

6. The plant according to claim 1, wherein the preparation module comprises at least one static mixer, wherein each static mixer is designed to homogenize mixtures for forming the first fluid, the second fluid and/or, if appropriate, the intermediate fluid.

7. The plant according to claim 1, wherein the production device comprises at least one element chosen from:
    a nozzle
    a mixer provided with at least one dispersion module, and
    a static mixer.

8. The plant according to claim 7, wherein the production device comprises at least a plurality of nozzles, wherein first rails and second rails, and, where appropriate, third rails, are each connected to the plurality of nozzles, wherein the nozzles are preferably arranged in parallel with each other.

9. The plant according to claim 7, wherein each distribution rail is connected to the corresponding nozzle by a connection forming a pressure drop.

10. The plant according to claim 1, wherein the plant comprises a collector connected to the production device and capable of collecting the composition.

11. The plant according to claim 10, wherein the production device and/or the collector comprises at least one injection device of a solution for increasing the viscosity of the second fluid.

12. The plant according to claim 11, wherein a rail for distribution of a solution for increasing the viscosity is connected to each nozzle in order to inject the solution for increasing viscosity in the second fluid after the formation of drops.

13. A method for producing a composition, comprising drops of at least one first fluid dispersed in a second fluid that is substantially immiscible with the first fluid, wherein each drop comprises a core formed of the first fluid from a plant according to claim 1, wherein the method comprises:
    the preparation, in the preparation module:
        of the first fluid by mixing determined quantities of the first stock solution and at least a first solution of active agent(s) and/or additional compound(s), and
        of the second fluid by mixing determined quantities of the second stock solution,
    the simultaneous or sequential conveying of the first fluid, the second fluid and, if appropriate, the intermediate fluid in the production device, and
    the formation of a composition by the production device.

14. The method according to claim 13, wherein the method further comprises, after the step of forming the composition:
    the preparation in the same preparation module of at least one additional fluid different from the first fluid and/or of at least one second additional fluid different from the second fluid, and
    the simultaneous or sequential conveying of the first additional fluid, the second additional fluid, and
    the formation of an additional composition by the production device.

15. The method according to claim 13, wherein the method further comprises, after the step of forming the composition, a step of injecting a solution for increasing the viscosity of the composition, especially the second fluid.

16. A process of personalizing a composition by a consumer, comprising a step of using the plant according to claim 14.

17. The plant according to claim 7, wherein the nozzle comprises a hollow body delimiting an internal duct and an external duct extending along a vertical longitudinal axis and arranged in a coaxial manner along the longitudinal axis, wherein the external duct opens downwards through an opening forming drops,
- wherein the nozzle comprises a first external feed duct of the first fluid and a second external feed duct of the second fluid,
- wherein the first external feed duct is connected to the internal duct, while the second external feed duct is connected to the external duct.

18. The plant according to claim 1, wherein each drop comprises a shell that is designed to retain the core,
- wherein the storage module comprises at least one storage tank of at least a third stock solution,
- wherein the preparation module is designed to prepare an intermediate fluid by mixing determined quantities of the third stock solution,
- wherein the preparation module is suitable for conveying, the intermediate fluid.

19. The plant according to claim 18, wherein the storage module further comprises, at least one storage tank of at least one third solution of active agent(s) and/or additional compound(s),
- wherein the preparation module is designed to prepare the intermediate fluid by mixing, determined quantities of the third stock solution and of at least the third solution of active agent(s) and/or additional compound(s), and
- wherein the control unit is designed to determine the quantity of the third stock solution to be mixed with a determined quantity of one or more third solutions of active agent(s) and/or additional compound(s) to obtain the intermediate fluid.

20. The plant according to claim 1, wherein the storage module further comprises at least one storage tank of at least one second solution of active agent(s) and/or additional compound(s),
- wherein the preparation module is designed to prepare the second fluid by mixing, determined quantities of the second stock solution and of at least the second solution of active agent(s) and/or additional compound(s), and
- wherein the control unit is designed to determine the quantity of one or more second solutions of active agent(s) and/or additional compound(s) to be mixed with the determined quantity of the second stock solution to obtain the second fluid.

21. The plant according to claim 3, wherein the storage module comprises several tanks containing several perfume solutions, and wherein the preparation module is able to mix selectively a determined quantity of one or more perfume solutions(s) to form the first fluid and/or the second fluid.

22. The plant according to claim 21, wherein the storage module comprises several tanks containing several third solutions of active agent(s) and/or additional compound(s), and wherein the preparation module is able to mix selectively a determined quantity of one or more third solutions of active agent(s) and/or of additional compound(s) with a determined quantity of third stock solution and a determined quantity of one or several perfume solutions for forming the intermediate fluid.

23. The plant according to claim 17, wherein the nozzle further comprises a third external feed duct of the intermediate fluid, connected to the internal duct.

* * * * *